(12) United States Patent
Ishii et al.

(10) Patent No.: US 6,960,460 B2
(45) Date of Patent: Nov. 1, 2005

(54) ESTERASE GENE AND ITS USE

(75) Inventors: Takeshi Ishii, Takarazuka (JP); Satoshi Mitsuda, Takarazuka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 391 days.

(21) Appl. No.: 10/147,467

(22) Filed: May 17, 2002

(65) Prior Publication Data

US 2003/0027295 A1 Feb. 6, 2003

Related U.S. Application Data

(60) Division of application No. 09/219,120, filed on Dec. 23, 1998, now Pat. No. 6,472,189, which is a continuation-in-part of application No. 08/978,589, filed on Nov. 26, 1997, now Pat. No. 6,087,145.

(30) Foreign Application Priority Data

Nov. 28, 1996 (JP) ............................................. 8-318274
Dec. 24, 1996 (JP) ............................................. 8-344076

(51) Int. Cl.$^7$ ................................................ C12N 9/18
(52) U.S. Cl. ...................................... 435/197; 435/196
(58) Field of Search ................................. 435/196, 197

(56) References Cited

U.S. PATENT DOCUMENTS

| | | | |
|---|---|---|---|
| 4,607,013 A | 8/1986 | Mitsuda et al. | |
| 5,290,694 A | 3/1994 | Nakanishi et al. | |
| 5,306,636 A | 4/1994 | Iizumi et al. | |

FOREIGN PATENT DOCUMENTS

| | | |
|---|---|---|
| EP | 0 487 541 B1 | 6/1992 |
| EP | 657535 A2 | 6/1995 |
| JP | 6-153965 A | 6/1994 |
| JP | 7-504561 A1 | 5/1995 |

OTHER PUBLICATIONS

Jorgensen et al., Journal of Bacteriology, vol. 173, No. 2, (1991), pp. 559–567.

Sugihara et al., J. Biochem., vol. 112, (1992), pp. 598–603.

Kinoshita et al., Factors influencing enantioselectivity of lipase–catalyzed hydrolysis, Tetrahedron, vol. 52, No. 15, (1996), pp. 5397–5406.

Hirose et al., Inversion of enantioselectivity in hydrolysis of 1,4–dihydropyridines by point mutation of lipase PS. Tetrahedron Lett., vol. 36, No. 7, (1995), pp. 1063–1066.

Sih et al., Differences in reactivity and enantioselectivity in Lipase reactions with carboxylic esters and alcohols bearing the same stereogenic center. Tetrahedron:Assymetry, vol. 6, (1995), pp. 357–360.

Schrag et al., Structure, vol. 5, No. 2, (1997), pp. 187–202.

Frenken et al., Applied and Environmental Microbiology, vol. 58, No. 12, (Dec. 1992), pp. 3787–3791.

*Primary Examiner*—Gabriele E. Bugaisky
(74) *Attorney, Agent, or Firm*—Birch, Stewart, Kolasch & Birch, LLP

(57) ABSTRACT

An isolated esterase gene coding for an esterase capable of causing asymmetric hydrolysis of an organic carboxylic acid ester of a cyclopentenolone of formula I:

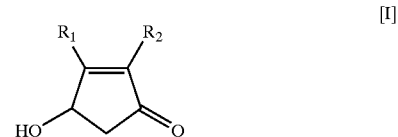

wherein $R_1$ is hydrogen or methyl, and $R_2$ is $C_1$–$C_{10}$ alkyl, $C_2$–$C_{10}$ alkenyl, $C_2$–$C_{10}$ alkynyl, $C_1$–$C_4$ haloalkyl, a $C_5$–$C_9$ aliphatic hydrocarbon moiety which may be optionally protected on the terminal hydroxyl group thereof, or a $C_5$–$C_9$ fatty acid residue which may be optionally protected on the terminal carboxyl group thereof, to produce the cyclopentenolone of formula I in (R)-form, and hybridizing to the base sequence of SEQ ID NO:1, is useful for the industrially favorable production of optically active cyclopentenolones of formula I which serve as the intermediates of drugs, agricultural chemicals or other active products.

6 Claims, 1 Drawing Sheet

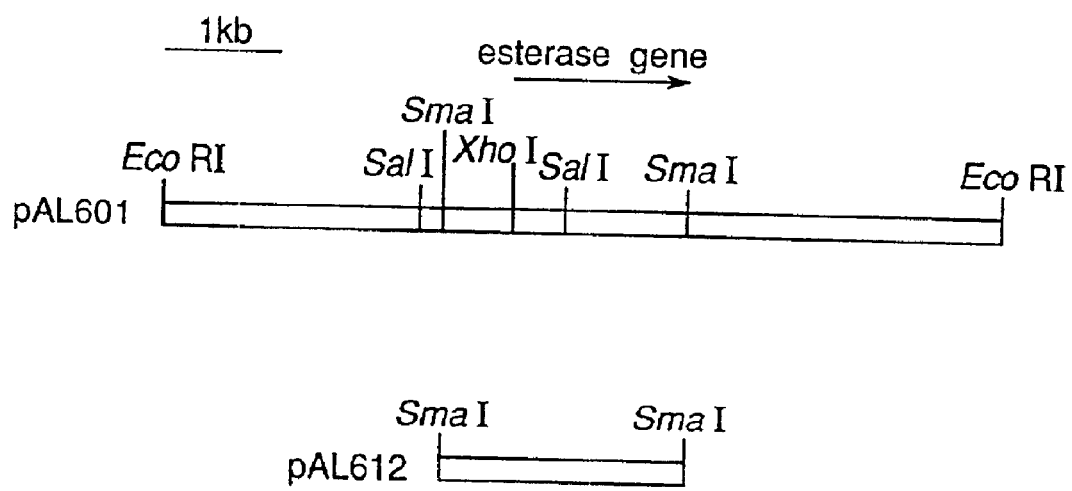

ESTERASE GENE AND ITS USE

CROSS REFERENCE TO RELATED APPLICATION

This application is a divisional application of application Ser. No. 09/219,120, filed on Dec. 23, 1998 now U.S. Pat. No. 6,472,189, which is a continuation-in-part of application Ser. No. 08/978,589 filed Nov. 26, 1997 now U.S. Pat. No. 6,087,145, the entire contents of both of which are hereby incorporated by reference and for which priority is claimed under 35 U.S.C. §120; and this application claims priority of Application No. 8-318274 and 8-344076 filed in Japan on Nov. 28, 1996 and Dec. 24, 1996, respectively under 35 U.S.C. § 119.

FIELD OF INVENTION

The present invention relates to an esterase gene and its use.

BACKGROUND OF THE INVENTION

Cyclopentenolones of formula I

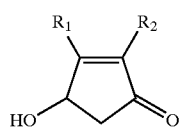

[I]

wherein $R_1$ is hydrogen or methyl, and $R_2$ is $C_1$–$C_{10}$ alkyl, $C_2$–$C_{10}$ alkenyl, $C_2$–$C_{10}$ alkynyl, $C_1$–$C_4$ haloalkyl, a $C_5$–$C_9$ hydroxy aliphatic hydrocarbon moiety which may be optionally protected on the terminal hydroxyl group thereof, or a $C_5$–$C_9$ fatty acid residue which may be optionally protected on the terminal carboxyl group thereof, are important as the intermediates of drugs, agricultural chemicals or other active products These cyclopentenolones are useful as the important alcohol components in a group of ester compounds, commonly called "synthetic pyrethroids," having excellent insecticidal activity, and they are also useful as the intermediates of prostaglandin derivatives which serve as drugs.

For example, the compound of formula II below, an ester of 4-hydroxy-3-methyl-2-(2-propynyl)cyclopent-2en-1-one with 2,2,3,3-tetramethylcyclopropanecarboxylic acid, is an excellent insecticide having very strong knockdown activity and mortal activity (see, e.g., JP-B 50-15843/1975).

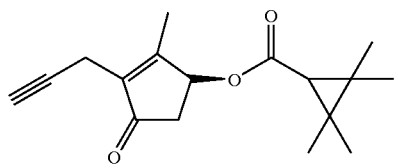

[II]

The cyclopentenolones of formula I include two kinds of optical isomers because they have an asymmetric carbon atom at position 4. In the case of synthetic pyrethroids containing such optical isomers as the alcohol components, it is well known that the difference in optical isomerism between these alcohol components makes a great difference in their insecticidal effects. For example, the compound of formula II above has been found to exhibit several times as excellent insecticidal activity in the case of an ester of (S)-4-hydroxy-3-methyl-2-(2-propynyl)cyclopent-2-en-1-one as in the case of an ester of the corresponding (R)4-hydroxy-3-methyl-2-(2-propynyl)cyclopent-2-en-1-one.

Furthermore, similar optically active cyclopentenolones of formula I, such as 4-hydroxy-2-(7-hydroxyheptyl)-2-cyclopentenone, 4-hydroxy-2-(6-methoxycarbonylhexyl)-2-cyclopentenone and 4hydroxy-2-(2-propenyl)-2-cyclopentenone, are useful as the intermediates of prostaglandin derivatives which serve as drugs.

For these reasons, there has been a great demand for the development of a method for separating and obtaining the optical isomers of cyclopentenolones of formula I as the intermediates of drugs, agricultural chemicals or other active products in an industrially favorable manner. In addition, for this purpose, in order to prepare a microorganism, for example, by a gene engineering technique, which microorganism can produce an excellent esterase capable of acting upon an organic carboxylic acid ester of a cyclopentenolone of formula I for asymmetric hydrolysis of the ester, the search of a gene coding for such an esterase has also been eagerly desired.

SUMMARY OF THE INVENTION

Under these circumstances, the present inventors have extensively studied and found an esterase gene coding for an esterase capable of acting upon an organic carboxylic acid ester of a cyclopentenolone of formula I for asymmetric hydrolysis of the ester to produce the cyclopentenolone in (R)-form with high optical purity, thereby completing the present invention.

Thus, the present invention provides:

1) An isolated esterase gene coding for an esterase capable of causing asymmetric hydrolysis of an organic carboxylic acid ester of a cyclopentenolone of formula I:

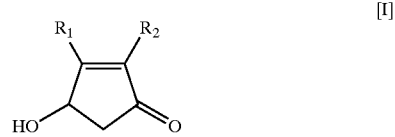

[I]

wherein $R_1$ is hydrogen or methyl, and $R_2$ is $C_1$–$C_{10}$ alkyl, $C_2$–$C_{10}$ alkenyl, $C_2$–$C_{10}$ alkynyl, $C_1$–$C_4$ haloalkyl, a $C_5$–$C_9$ hydroxy aliphatic hydrocarbon moiety which may be optionally protected on the terminal hydroxyl group thereof, or a $C_5$–$C_9$ fatty acid residue which may be optionally protected on the terminal carboxyl group thereof, to produce the cyclopentenolone of formula I in (R)-form, and hybridizing to the base sequence of SEQ ID NO:1 (hereinafter referred to as the present gene);

2) The isolated esterase gene according to item 1, wherein the homology of the gene to the base sequence of SEQ ID NO:1 is 90% or higher.

3) The isolated esterase gene according to item 1, having a base sequence coding for the amino acid sequence of SEQ ID NO:2.

4) The isolated esterase gene according to item 1, having the base sequence of SEQ ID NO:1.

5) A plasmid containing the isolated esterase gene of item 1, 2, 3 or 4 (hereinafter referred to as the present plasmid).

6) A transformant obtained by transformation with the plasmid of item 5 (hereinafter referred to as the present transformant).

7) The transformant according to item 6, which is a microorganism.

8) An esterase produced by a microorganism having the isolated esterase gene of item 1, 2, 3 or 4 (hereinafter referred to as the present esterase).

9) The esterase according to item 8, wherein the microorganism having the isolated esterase gene of item 1, 2, 3 or 4 is the transformant of item 6.

10) A process for producing en esterase, which comprises cultivating the transformant of item 6 to produce an esterase capable of causing asymmetric hydrolysis of an organic carboxylic acid ester of a cyclopentenolone of formula I:

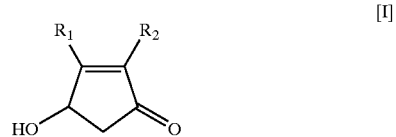

[I]

wherein $R_1$ is hydrogen or methyl, and $R_2$ is $C_1$–$C_1$ alkyl, $C_2$–$C_{10}$ alkenyl, $C_2$–$C_{10}$ alkynyl, $C_1$–$C_4$ haloalkyl, a $C_5$–$C_9$ hydroxy aliphatic hydrocarbon moiety which may be optionally protected on the terminal hydroxyl group thereof, or a $C_5$–$C_9$ fatty acid residue which may be optionally protected on the terminal carboxyl group thereof, to produce the cyclopentenolone of formula I in (R)-form (hereinafter referred to as the present production process).

11) A method for the optical resolution of a cyclopentenolone of formula I:

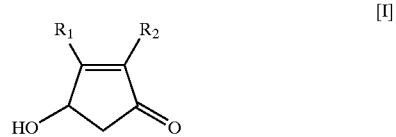

[I]

wherein $R_1$ is hydrogen or methyl, and $R_2$ is $C_1$–$C_{10}$ alkyl, $C_2$–$C_{10}$ alkenyl, $C_2$–$C_{10}$ alkynyl, $C_1$–$C_4$ haloalkyl, a $C_5$–$C_9$ aliphatic hydrocarbon moiety which may be optionally protected on the terminal hydroxyl group thereof, or a $C_5$–$C_9$ fatty acid residue which may be optionally protected on the terminal carboxyl group thereof, which comprises allowing the esterase of item 8 to act upon an organic carboxylic acid ester of the cyclopentenolone of formula I for asymmetric hydrolysis of the ester; and separating the cyclopentenolone of formula I in (R)-form from the ester of the corresponding enantiomer thereof.

12) The optical resolution method according to item 11, wherein the cyclopentenolone of formula I is 4-hydroxy-3-methyl-2-(2-propenyl)cyclopent-2-en-1-one.

13) The optical resolution method according to item 11, wherein the cyclopentenolone of formula I is 4-hydroxy-3-methyl-2-(2-propynyl)cyclopent-2-en-1-one.

BRIEF DESCRIPTION OF THE DRAWING

The sole FIGURE is a diagram showing the restriction endonuclease maps of pAL601 and pAL612, which are specific examples of the present plasmids.

DETAILED DESCRIPTION OF THE INVENTION

The present gene is an isolated esterase gene coding for an esterase capable of causing asymmetric hydrolysis of an organic carboxylic acid ester of a cyclopentenolone of formula I to produce the cyclopentenolone of formula I in (R)-form, and hybridizing to the base sequence of SEQ ID NO:1. The term "esterase" as used herein refers to an esterase as defined in a broad sense containing lipases.

The phrase "capable of causing asymmetric hydrolysis of an organic carboxylic acid ester of a cyclopentenolone of formula I to produce the cyclopentenolone of formula I in (R)-form" as used herein means that an esterase referred to by this phrase can cause asymmetric hydrolysis of an organic carboxylic acid ester of a cyclopentenolone of formula I, such as 4-hydroxy-3-methyl-2-methylcyclopent-2-en-1-one, 4-hydroxy-3-methyl-2-ethyl-2-cyclopent-2-en-1-one, 4hydroxy-3-methyl-2-(2-propenyl)-2-cyclopent-2-en-1-one, 4-hydroxy-3-methyl-2-(2,4-pentadienyl)-2-cyclopent-2en-1-one, 4hydroxy-3-methyl-2-(1-methyl-2-propynyl)-2-cyclopent-2-en-1-one, 4hydroxy-3-methyl-2-(2-propynyl)cyclopent-2-en-1-one, 4-hydroxy-3-methyl-2-(1-methyl-2-propynyl)cyclopent-2en-1-one, 4-hydroxy-3-methyl-2-(2,2,2-trifluoroethyl)cyclopent-2-en-1-one, 4-hydroxy-2-(7-acetoxyheptyl)-2-cyclopentenone, 4-hydroxy-2-(7-hydroxyheptyl)-2-cyclopentenone, 4-hydroxy-2-(6-methoxycarbonylhexyl)-2-cyclopentenone or 4-hydroxy-2-(2-propenyl)-2-cyclopentenone, to produce the corresponding cyclopentenolone in (R)-form.

In the cyclopentenolone of formula I, variables have the following meanings.

The $C_1$–$C_{10}$ alkyl represented by $R_2$ may include, for example, methyl ethyl, pentyl, heptyl and decyl.

The $C_2$–$C_{10}$ alkenyl represented by $R_2$ may include, for example, 2-propenyl, 1-methyl-2-propenyl, 2,4pentadienyl, 2-heptenyl and 2-decenyl.

The $C_2$–$C_{10}$ alkynyl represented by $R_2$ may include, for example, 2-propynyl, 1-methyl-2-propynyl, 2-heptynyl and 2-decynyl.

The $C_1$–$C_4$ haloalkyl represented by $R_2$ may include, for example, 2,2,2-tri-fluoroethyl and 4,4,4-trifluorobutyl.

The $C_5$–$C_9$ hydroxy aliphatic hydrocarbon moiety which may be optionally protected on the terminal hydroxyl group thereof may include $C_5$–$C_9$ hydroxy aliphatic hydrocarbon moieties which may be optionally protected on the terminal hydroxy groups thereof with, for example, alkyl or alkoxyalkyl. Particularly preferred are such substituents that aliphatic hydrocarbons contained therein are straight chain saturated aliphatic hydrocarbons, specific examples of which are 7-acetoxypentyl, 7-hydroxypentyl, 7-acetoxyheptyl, 7-hydroxyheptyl and 10-hydroxynonyl.

The $C_5$–$C_9$ fatty acid residue which may be optionally protected on the terminal hydroxyl group thereof may include $C_5$–$C_9$ fatty acid residues which may be optionally protected on the terminal hydroxyl group thereof with, for example, alkyl. Particularly preferred are such substituents that fatty acids contained therein are straight chain saturated fatty acids, specific examples of which are 6-methoxycarbonylhexyl and 8-methoxycarbonyloctyl.

In the above organic carboxylic acid ester, the organic carboxylic acid may include, for example, $C_1$–$C_{18}$ saturated or unsaturated fatty acids, and pyrethroid acids.

The gene "hybridizing to the base sequence of SEQ ID NO:1" refers to a gene which can be visually detected by Southern hybridization as described, for example, in "Cloning and Sequence" (complied under the supervision of Itaru Watanabe, edited by Masahiro Sugiura, 1989, published by Noson Bunka-sha), using DNA having the base sequence of SEQ ID NO:1 as a probe. The gene may be DNA having the base sequence of SEQ ID NO:1 or DNA having a base sequence with the addition, deletion or replacement of one or more bases in the DNA having the base sequence of SEQ ID NO:1. For example, double-stranded DNA is dissociated into the complementary single-stranded DNAs by heat treatment at 95° C. for 1 minute or by alkali treatment with 0.5 M NaOH, 1.5 M NaCl, which are then left cooling on ice for 1 minute or subjected to neutralization with 0.5 M Tris-HCl (pH 7.0), 3.0 M NaCl, so as to associate with single-stranded DNA or single-stranded RNA, which is complementary to the above single-stranded DNAs, to fall into a double-stranded state (i.e., hybridized state) again. Such DNA may be usually a gene having a base sequence with a high homology (e.g., about 90% or higher homology as a whole, although it may vary depending upon whether the region is closely related to an active site or a structure) to the base sequence of SEQ ID NO:1.

Homologies can be calculated with the homology search program developed by Pearson and Lipman (see, e.g., Pearson and Lipman, (1988), Proc. Natl. Acad. Sci. USA, 85, 2444). They can also be calculated with this kind of program contained in the Genetyx-Mac (available from Software Kaihatsu). For this purpose, a homology search program (fasta) found in the World Wide Web Service of the DNA Data Bank of Japan (DDBJ) can also be used.

A more specific example of the present gene is an esterase gene having a base sequence coding for the amino acid sequence of SEQ ID NO:2. Of course, the present gene may also include an esterase gene having the base sequence of SEQ ID NO:1.

The present gene can be obtained by the PCR method using genomic DNA prepared, for example, from a microorganism of the genus *Burkholderia* by an ordinary method (e.g., the method described in "Shin Saibo Kogaku Jikken Protocol" (edited by the Cancer Control Research Group, Medical Science Laboratory, Tokyo University, published by Shujun-sha, 1993) as a template and using a fragment of DNA having the base sequence of SEQ ID NO:1 (e.g., a combination of about 14 bp or more oligonucleotides complementary to the 5'-terminal sequence in the base sequence of SEQ ID NO:1 and about 14 bp or more oligonucleotides corresponding to the 3'-terminal sequence in the base sequence of SEQ ID NO:1; or a combination of about 14 bp or more oligonucleotides corresponding to the 5'-terminal sequence in the base sequence of SEQ ID NO:1 and about 14 bp or more oligonucleotides complementary to the 3'-terminal sequence in the base sequence of SEQ ID NO:1) as a primer.

The present gene can also be obtained by a method such as colony hybridization or plaque hybridization with a gene library constructed by the insertion of genomic DNA prepared, for example, from a microorganism of the genus *Burkholderia* by an ordinary method (e.g., the method described in "Shin Saibo Kogaku Jikken Protocol" (edited by the Cancer Control Research Group, Medical Science Laboratory, Tokyo University, published by Shujun-sha, 1993) into λ phages or plasmids, using a base sequence coding for the amino acid sequence of SEQ ID NO:2, preferably a 15 bp or more DNA fragment contained in the base sequence of SEQ ID NO:1, as a probe.

As the microorganism for use in the preparation of the present gene, among the microorganisms of the above genus, particularly preferred is *Burkholderia cepacia*, a specific example of which is *Burkholderia cepacia* strain SC-20.

*Burkholderia cepacia* strain SC-20 is a microorganism that has been found from the nature by the present inventors, and it has the bacteriological characteristics as shown in Table 1.

TABLE 1

| (1) Morphology | Rods |
|---|---|
| (2) Gram staining | Negative |
| (3) Spore | − |
| (4) Motility | + |
| (5) Flagellar arrangement | Single polar |
| (6) Attitude to oxygen | Aerobic |
| (7) Oxidase test | + |
| (8) Catalase test | + |
| (9) OF test | O (oxidation) |
| (10) Tone of colonies | Yellow |
| (11) Fluorescent pigment formation | − |
| (12) Water-soluble pigment formation | + |
| (13) PHB accumulation | + |
| (14) Protocatechuate cleavage | ortho |
| (15) Arginine dehydrolase | − |
| (16) Growth at 40° C. | + |
| (17) Denitrification | − |
| (18) Nitrate reduction | − |
| (19) Gelatin liquefaction | + |
| (20) Starch hydrolysis | − |
| (21) Utilization of: | |
| (a) Glucose | + |
| (b) Xylose | + |
| (c) Ribose | + |
| (d) Rhamnose | + |
| (e) Levulinate | + |
| (f) Mesaconate | − |
| (g) D-Tartrate | − |
| (h) 2,3-Butylene glycol | + |
| (i) Tryptamine | − |
| (22) Quinone type | Q-8 |
| (23) GC content of DNA in bacterial cells (mol %) | 68 |

These bacteriological characteristics are found to be consistent with those of *Burkholderia cepacia* when compared with the data in Bergey's Manual of Systematic Bacteriology, Vol. 1 (1984); Bergey's Manual of Determinative Bacteriology, Ninth edition (1994); Zhao et al., Int. J. Syst. Bacteriol., 45, p. 600 (1995); and Yabuuchi et al., Microbiol. Immnunol., 36, p. 1251 (1992).

The present gene can be obtained by the PCR method using DNA prepared from the bacterial cells of *Escherichia coli* strain JM109/pAL612 as a template and using a fragment of DNA having the base sequence of SEQ ID NO:1 (e.g., a combination of about 14 bp or more oligonucleotides complementary to the 5'-terminal sequence in the base sequence of SEQ ID NO:1 and about 14 bp or more oligonucleotides corresponding to the 3'-terminal sequence in the base sequence of SEQ ID NO:1; or a combination of about 14 bp or more oligonucleotides corresponding to the 5'-terminal sequence in the base sequence of SEQ ID NO:1 and about 14 bp or more oligonucleotides complementary to the 3'-terminal sequence in the base sequence of SEQ ID NO:1) as a primer.

*E. coli* strain JM109/pAL612 is a transformant microorganism obtained by the incorporation of plasmid pAL612 containing the present gene (the present plasmid) into *E. coli* strain JM109 (the present transformant), and it has been deposited in the National Institute of Bioscience and Human-Technology, Agency of Industrial Science and Technology as "FERM-BP 5740"(accession date: Nov. 7, 1996).

An original deposit of microorganism *Escherichia coli* JM109/pAL612 was made under the Budapest Treaty on Nov. 7, 1996 at the National Institute of Bioscience and Human-Technology Agency of Industrial Science and Technology 1-3 Higashi 1 Chome Tsukuba-shi Ibaraki-ken, 305 JAPAN. The accession number given by the International depositary authority is FERN BP-5740. The deposit will be made irrevocably available to the public upon the issuance of the patent.

The present plasmid can be easily constructed by incorporating the present gene obtained, for example, into a vector which has been usually used in host cells to be transformed, by an ordinary gene engineering technique. More specifically, for example, when E. coli as a microorganism is used as the host cell, the vector to be used may include pUC119 (available from Takara Shuzo) and pBluescriptII (available from Stratagene Cloning System).

The method for transforming a host cell with the present plasmid constructed may be a method usually used depending upon the host cell to be transformed, and for example, when E. coli as a microorganism is used as the host cell, it may include an ordinary method as described in "Molecular Cloning" (J. Sambrook et al., Cold Spring Harbor, 1989).

The selection of transformants is carried out as follows: For example, the host cell transformed with the present plasmid is first cultivated on an LB plate containing tributyrin, and those forming a clear zone are selected. The selected transformants are cultivated, and the resulting cultures are treated with an organic carboxylic acid ester of a cyclopentenolone of formula I. The reaction products are analyzed, so that transformants producing the cyclopentenolone of formula I in (R)-form with high optical purity may be selected.

More specifically, for example, 0.5 g of the acetic acid ester of (RS)-4-hydroxy-3-methyl-2-(2-propenyl)cyclopent-2-en-1-one and 8.0 ml of 50 mM phosphate buffer (pH 7.0) are put into a 100 ml sample bottle, and the mixture is preheated at 40° C. under stirring with a stirring bar for 10 minutes. To this mixture is added 1.0 ml of the above culture, and the reaction is effected at 40° C. under stirring with a stirring bar. After 30 minutes, the reaction mixture is taken in a volume of 50 µl, and the reaction is stopped by the addition of 1 ml of ethanol. For blanks, purified water is used instead of the culture, and the test is conducted in the same manner. The rate of decomposition is determined by gas chromatography. As the column for analysis, 10% silicone DC-QF-1, 2.6 m long, is used, and the analysis is carried out with GC-14A (available from Shimazu Seisakusho) under the following conditions: column temperature, 150° C.; injection temperature, 170° C.; detection temperature, 170° C.; and detector, FID. For the enzyme titer, the amount of enzyme releasing 1 µmol of (R)-4 hydroxy-3-methyl-2-(2-propenyl)-cyclopent-2-en-1-one for 1 minute is defined as 1 unit. The reaction mixture is further extracted with methyl isobutyl ketone, and the extract is examined for the optical purity of (R)-4-hydroxy-3-methyl-2-(2-propenyl)cyclopent-2-en-1-one by the HPLC analysis. In the analysis, columns for optical isomer analysis OA4100 (4.0 mm I.D.×25 cm) available from Sumika Bunseki Center are used. As the eluent, a mixture of hexane, 1,2-dichloroethane and ethanol at a ratio of 100:20:1 can be used. The optical isomer ratio may be determined at a flow rate of 1.0 ml/min. with an absorbance at 230 nm as an index.

More particularly, from the selected transformants, plasmids contained in the transformants are prepared, and the restriction endonuclease maps of the plasmids thus prepared are constructed by an ordinary method as described, for example, in "Molecular Cloning" (J. Sambrook et al., Cold Spring Harbor, 1989). It can also be determined whether the desired present gene is contained or not by a method such as base sequence analysis, Southern hybridization or Western hybridization.

In this manner, the present transformants can be obtained and cultivated to produce the present esterase (the present production process).

When the transformants are microorganisms, the transformants are cultivated with various kinds of media suitably containing carbon sources, nitrogen sources, organic salts and/or inorganic salts, and other additives, which have been used for preparing the ordinary cultures of microorganisms. The carbon sources may include glucose, glycerol, dextrin, sucrose, organic acids, animal and vegetable oils, and molasses. The nitrogen sources may include organic and inorganic nitrogen sources such as broth, peptone, yeast extract, malt extract, soy bean powder, corn steep liquor, cotton seed powder, dry yeast, casamino acid, sodium nitrate and urea. The organic and inorganic salts may include chlorides, sulfates, acetates, carbonates and phosphates of elements such as potassium, sodium, magnesium, iron, manganese, cobalt and zinc, specific examples of which are sodium chloride, potassium chloride, magnesium sulfate, ferrous sulfate, manganese sulfate, cobalt chloride, zinc sulfate, copper sulfate, sodium acetate, calcium carbonate, sodium carbonate, potassium monohydrogenphosphate and potassium dihydrogenphosphate.

Furthermore, the addition of triglycerides such as olive oil to the medium is preferred. The amount of triglycerides to be added may be about 10 mg to about 10 g for each 100 ml of the medium.

Cultures are prepared by an ordinary method for microorganisms, and they can be in the form of either solid cultures or liquid cultures (e.g., shaking cultures using test tubes or reciprocating shakers, and other cultures using jar fermenters or fermentation tanks). In particular, when jar fermenters are used, it is necessary to introduce aseptic air thereinto, usually at a rate of about 0.1 to about 2 times the culture volume per minute. The incubation temperature may be suitably altered within a range to ensure the growth of microorganisms. For example, cultures are preferably incubated at a temperature of about 15° C. to about 40° C. under the control of medium pH within the range of about 6.0 to about 8.0. The incubation period may vary on various conditions of incubation, and the preferred incubation period is usually in the range of about 1 to about 5 days.

The present esterase has the following characteristics:

1) The molecular weight (determined by SDS-PAGE) is about 38 kilo-daltons;

2) The isoelectric point (pI) is 6.0;

3) The optimum temperature is about 60° C., and the reaction can be effected in the range of at least about 20° C. to about 70° C., preferably about 30° C. to about 40° C.;

4) The reaction can be effected in the pH range of about 4 to about 9, preferably about 5 to about 7;

5) It is capable of causing asymmetric hydrolysis of an organic carboxylic acid ester of a cyclopentenolone of formula I to produce the cyclopentenolone of formula I in (R)-form;

6) It can also be obtained by cultivating non-transformants, for example, of a microorganism of the genus Burkholderia (particularly preferred is Burkholderia cepacia, a specific example of which is Burkholderia cepacia stain SC-20). Of course, as described above, it can also be obtained by cultivating the transformants which have been prepared by transformation with a plasmid containing the present gene.

The present esterase may be utilized for the enzyme reaction in the form of a culture containing the same, but may also be utilized for the enzyme reaction in the form of a crude enzyme separated from the culture or in the form of a purified enzyme. The crude enzyme may be separated by an ordinary method, for example, in which bacterial cells are disrupted by ultrasonic disintegration, trituration with glass beads or alumina, homogenization or disruption with a French press, enzyme treatment with lysozyme, and the desired fraction is obtained from the disrupted bacterial cells by salt deposition with ammonium sulfate or any other salt; precipitation with an organic solvent or an organic polymer such as polyethylene glycol; chromatography such as ion exchange chromatography, hydrophobic chromatography, gel filtration chromatography, affinity chromatography or any other chromatography; or electrophoresis. If necessary, these techniques can be used in combination.

Furthermore, the present esterase can also be utilized for the enzyme reaction in the form of an immobilized product which has been obtained by insolubilizing the esterase by a method of immobilization, such as a carrier binding technique in which the esterase is attached to a carrier by covalent bonding, ion bonding or absorption; or an entrapment technique in which the esterase is entrapped into the network structure of a polymer; and then by processing the insolubilized esterase into an easily separable state.

The present esterase can be utilized, for example, in the optical resolution of a cyclopentenolone of formula I. That is, the present esterase can be allowed to act upon an organic carboxylic acid ester of a cyclopentenolone of formula I for asymmetric hydrolysis of the ester, so that the cyclopentenolone of formula I in (R)-form is separated from the ester of the corresponding enantiomer thereof in (S)-form. In such a resolution, esters in racemic form are usually used as the starting material.

Specific examples of the cyclopentenolone of formula I are 4hydroxy-3-methyl-yl-2-(2-propenyl)cyclopent-2-en-1-one, 4hydroxy-3-methyl-2-(2-propynyl)cyclopent-2-en-1-one, 4-hydroxy-2-(7-hydroxyheptyl)-2-cyclopentenone, 4-hydroxy-2-(6-methoxycarbonylhexyl)-2-cyclopentenone and 4-hydroxy-2-(2-propenyl)-2-cyclopentenone.

The reaction temperature is, for example, in the range of about 20° C. to about 70° C., preferably about 30° C. to about 40° C. The reaction pH is, for example, in the range of about 4 to about 9, preferably about 5 to about 7. The reaction time is, for example, in the range of about 5 minutes to about 96 hours.

The cyclopentenolone of formula I in (R)-form and the ester of the corresponding enantiomer thereof can be recovered from the reaction mixture by any method generally known in the art. For example, procedures such as extraction with a solvent, fractional distillation and column chromatography can be suitably employed. More specifically, the reaction mixture is extracted with an organic solvent such as ether, ethyl acetate or benzene, and the extract is subjected to factional distillation, or to silica gel chromatography, followed by extraction, so that the cyclopentenolone of formula I in (R)-form is separated from the ester of the corresponding enantiomer thereof. Thus, the desired synthetic pyrethroids or prostaglandin derivatives can be obtained from the separated products.

The cyclopentenolone of formula I in (R)-form thus recovered can be easily converted into the cyclopentenolone of formula I in (S)-form, which is important as the alcohol intermediate of synthetic pyrethroids or as the intermediate of prostaglandin derivatives, by direct hydrolysis or by hydrolysis after tosylation or mesylation according to any one of the methods described in JP-A 52-156840/1977, JP-B 4-5019/1992 and JP-B 5-36429/1993 depending upon the purpose of use, for optical reversal to change into the corresponding enantiomer. The cyclopentenolone thus obtained can be used, for example, by esterification, to produce the desired synthetic pyrethroids or prostaglandin derivatives.

The ester in (S)-form remaining after the asymmetric hydrolysis can be converted into the cyclopentenolone of formula I in (S)-form by direct hydrolysis, or by hydrolysis after the pre-hydrolysis or after the tosylation or mesylation of the reaction products of the asymmetric hydrolysis as described in JP-B 5-79656/1993. The cyclopentenolone of formula I in (S)-form can be used, for example, by esterification in the same manner as described above, to produce the desired synthetic pyrethroids or prostaglandin derivatives.

Thus, according to the present invention, the organic carboxylic acid esters of cyclopentenolones of formula I can also be entirely converted into the organic carboxylic acid esters of cyclopentenolones of formula I in (S)-form; the present production process is, therefore, extremely effective from an industrial point of view.

EXAMPLES

The present invention will be further illustrated by the following examples; however, the present invention is not limited to these examples in any way whatsoever.

Example 1 (Preparation of Genomic DNA)

A culture of *Burkholderia cepacia* strain SC-20 was grown on a medium (Bacto tryptone (available from Difco Laboratories Incorporated), 10 g; Bacto yeast extract (available from Difco Laboratories Incorporated), 5 g; NaCl, 5 g/l; hereinafter referred to simply as LB medium) at 30° C. for 12 hours, and then harvested by centrifugation at 6000 rpm for 10 minutes to collect the bacterial cells.

The collected bacterial cells were suspended in a solution (10 mM Tris-HCl (pH 8.0), 1 mM EDTA-NaOH (pH 8.0), 10 mM NaCl; hereinafter referred to simply as TEN solution) containing 1 mg/ml lysozyme chloride (available from Seikagaku Kogyo) and 25 $\mu$g/ml RNaseA (available from Sigma Aldrich Japan), and then incubated at 37° C. for 20 minutes. Thereafter, sodium dodecylsulfate was added to a final concentration of 1% (w/v), and incubation was continued at 55° C. for 10 minutes. Then, phenol saturated with TE [10 mM Tris-HCl (pH 8.0), 1 mM EDTA (pH 8.0)] was added in the same volume. The mixture was slowly stirred and then centrifuged at 10,000 rpm for 10 minutes to collect the upper layer, to which a TE-saturated phenol-chloroform solution was added in the same volume. The mixture was slowly stirred and then centrifuged at 10,000 rpm for 10 minutes to collect the upper layer, to which a 3M ammonium acetate solution was added in a ¹/₁₀-fold volume and then ethanol in a 2-fold volume. The DNA being deposited was taken by rolling it up round a glass rod. This DNA was rinsed with 70% (v/v) ethanol, and then rinsed again with 80% (v/v) ethanol and 100% ethanol, successively, followed by air drying. The DNA thus obtained was suspended in a TEN solution containing 25 $\mu$g/ml RNaseA (available from Sigma Aldrich Japan) and 20 $\mu$g/ml Proteinase K (available from Boehringer Manaheim), and then incubated at 37° C. for 12 hours, to which a TE-saturated phenol-chloroform solution was added in the same volume. The mixture was slowly stirred and then centrifuged at 10,000 rpm for 10 minutes to collect the upper layer, to which a 3M ammonium acetate solution was added in a ¹/₁₀-fold volume and then ethanol, in a 2-fold volume. The DNA being deposited was taken by rolling it up round a glass rod. This DNA was rinsed with 70% (v/v) ethanol, and then rinsed again with 80% (v/v) ethanol and 100% ethanol, successively, followed by air drying. The DNA thus obtained was dissolved in 10 ml of TE solution containing 25 µg/ml RNaseA, and the solution was dialyzed twice against 2 L of TE solution. Thus, about 1.6 mg of genomic DNA was obtained from 100 ml of the culture.

Example 2 (Preparation of Genomic DNA Library)

Fifty micrograms of the genomic DNA obtained above was digested with the restriction endonuclease Eco RI at 37° C. for 1 hour, followed by agarose gel electrophoresis (0.7% concentration). DNA fractions corresponding to the size of 9.4 kb to 6.6 kb and those corresponding to the size of 7.5 kb to 5.5 kb were cut out of the agarose gel, and then purified with Gene Clean (available from BIO101).

The purified DNA fragments and λZAPII DNA (available from Stratagene Cloning System) were ligated together with DNA ligase according to the manual attached to the kit. The ligated DNA was in vitro packaged into the λ particles using Gigapack Gold Packaging Kit (available from Stratagene Cloning System) according to the mnanual attached to the kit.

Example 3 (Preparation of Probe DNA)

(1) Purification of Esterase Enzyme

A culture of Burkholderia cepacia strain SC-20 isolated from the soil was grown on a medium (soy bean powder extract, 100 ml; corn steep liquor, 1 g; soy bean oil, 5 g) at 30° C. for 48 hours. The soy bean powder extract was prepared by adding 250 ml of 0.3% NaOH to 10 g of soy bean powder, heating the mixture at 70° C. for 1 hour, and filtering the mixture through a filter paper. After completion of the cultivation, the supernatant was collected by centrifugation at 14,000 rpm for 20 minutes. To the collected supernatant, ethanol was added to a concentration of 80%, and the precipitate was collected by further centrifugation at 14,000 rpm for 20 minutes.

The precipitate after drying was suspended in 50 mM phosphate buffer (pH 7.0), and fractions precipitating in an ammonium sulfate concentration of 20% to 60% were collected.

The collected fractions were suspended in 5 ml of 20 mM Tris-HCl (pH 8.0) solution, and the suspension was charged on a DEAE-Sepharose Fast Flow column (2.6×5 cm, available from Pharmacia Biotech) equilibrated with 20 mM Tris-HCl (pH 8.0) solution. The column was thoroughly washed with 20 mM Tris-HCl (pH 8.0) solution. After the washing, the desired protein was eluted by a gradient of NaCl concentration ranging from 0 M to 0.5 M, resulting in an active fraction. The active fraction obtained was purified in the same manner as described above using a DEAE-Sepharose Fast Flow column (2.6×5 cm, available from Pharmacia Biotech) equilibrated with 10 mM Tris-HCl (pH 7.5) solution, resulting in an active fraction. The active fraction obtained was purified by gel filtration chromatography using a Superose 12 HR10/30 column (available from Pharmacia) equilibrated with 50 mM phosphate buffer (pH 7.5) containing 150 mM NaCl.

The active fraction thus obtained (i.e., main peak) was capable of causing asymmetric hydrolysis of the acetic acid ester of (RS)-4-hydroxy-3-methyl-2-(2-propenyl)-cyclopent-2-en-1-one to produce (R)4-hydroxy-3-methyl-2-(2-propenyl)cyclopent-2-en-1-one. The active fraction was further capable of causing asymmetric hydrolysis of the acetic acid ester of (RS)-4-hydroxy-3-methyl-2-(2-propynyl)cyclopent-2-en-1-one to produce (R)4-hydroxy-3-methyl-2-(2-propynyl)cyclopent2-en-1-one. The analysis of the active fraction by SDS electrophoresis [using Automatic Electrophoresis Apparatus Phast System (available from Pharmacia Biotech) with Phast Gel Gradient 10–15 and Phast Gel SDS buffer strip] revealed that the active fraction is in a single state as a protein and that the protein is composed of a single subunit and has a molecular weight of about 38 kilo-daltons.

(2) Preparation of Probe DNA

The protein thus obtained was concentrated by ultrafiltration (available from Grace Japan) with a cut away molecular weight of 10 kilo-daltons, desalted on a desalting column (Fast Desalting Column, available from Pharmacia Biotech) equilibrated with water, and then concentrated under reduced pressure. The protein thus concentrated was digested from the N-terminus using Protein Sequencer 470A (available from Perkin Elmer Japan), and then analyzed with PTH-Analyzer 120A (available from Perkin Elmer Japan) to determine the N-terminal amino acid sequence. The amino acid sequence determined is shown by SEQ ID NO:3 in the Sequence Listing.

Based on the N-terminal amino acid sequence determined as described above, an oligonucleotide having the base sequence shown by SEQ ID NO:4 in the Sequence Listing was synthesized. For the synthesis of the oligonucleotide, DNA automatic synthesizer model 380A (available from Perkin Elmer Japan) was used. The synthesized DNA was labeled with a radioisotope using MEGALABEL kit (available from Takara Shuzo).

Example 4 (Isolation of Phage Containing the Present Gene)

The genomic DNA library prepared in Example 2 was screened for the present gene with Colony/Plaque Screen (available from NEN Research Products) according to the manual attached to the kit. More specifically, a culture of E. coli XL1-Blue was grown on an LB medium, and then harvested by centrifugation at 8000 rpm for 15 minutes to collect the bacterial cells. The bacterial cells collected were suspended in 10 mM $MgSO_4$ solution, and the bacterial suspension was then infected with λ phage containing the genomic DNA library prepared in Example 2. After the infection, the suspension was mixed with a medium (NaCl, 5 g/l; $MgSO_4$-$H_2O$, 2 g/l; Bacto yeast extract (available from Difco Laboratories Incorporated), 5 g/l; NZ amine, 10 g/l; herein-after referred to simply as NZY medium) containing 0.7% agarose and warmed to 50° C. The mixture was layered on an NZY agar plate of 150 mm in diameter. About twenty thousand phages were placed on each plate, and incubated at 37° C. until plaques appeared. After the incubation, the plaques formed on the plates were transferred to a Colony/Plaque Screen membrane at a ratio of two membranes per plate. The Colony/Plaque Screen membranes were treated twice with 0.5 M NaOH solution for 5 minutes, neutralized twice with 1.0 M Tris-HCl (pH 8.0) solution for 5 minutes, and then rinsed with 2×SSC solution, followed by air drying on filter paper. (The term "n×SSC solution" refers to a n/20-fold dilution of 20×SSC solution, and the "20×SSC solution" contains 175.3 g of NaCl and 88.2 g of trisodium citrate per liter (pH 7.0); hereinafter referred to simply as "n×SSC").

The Colony/Plaque Screen membranes obtained were immersed in 2×SSC, and then immersed in a prehybridization solution warmed to 68° C. for 3 hours, containing 6×SSC, 0.5% (w/v) sodium dodecyl sulfate (hereinafter referred to simply as "SDS"), 5× Denhart's solution (0.1 g of Ficoll, 0.1 g of polyvinylpyrrolidone, and 0.1 g of bovine serum albumin per 100 ml), and 100 µg/ml denatured sonicated sermon sperm DNA. The membranes thus pre-treated were then immersed in a hybridization solution containing 6×SSC, 0.5% (w/v) SDS, and 100 µg/ml denatured sonicated sermon sperm DNA, to which the probe DNA prepared in Example 3 was added, and the mixture was left under shaking at 63° C. for 18 hours. Thereafter, the membranes were washed with 2×SSC, 0.5% SDS solution at room temperature for 5 minutes. The membranes were further (1) washed under shaking with 2×SSC, 0.1% SDS solution at room temperature for 15 minutes, (2) washed under shaking with 0.1×SSC, 0.5% SDS solution at 37° C. for 60 minutes, and (3) washed under shaking with 0.1×SSC, 0.5% SDS solution at 68° C. for 60 minutes to remove excessive probe DNA. From the positions corresponding to the probe DNA adsorbed on the membranes, phases were taken by suction with a Pasteur pipette. The above procedures were repeated until the probe DNA was separated as a unique plaque, and phages containing the desired DNA fragment (the present gene) were isolated. Thus, about forty thousand plaques were screened, and three strains of phages were isolated.

Example 5 (Acquisition of Transformant and Analysis of Base Sequence)

The phages obtained in Example 4 were recombined into a plasmid according to the manual of λ ZAPII (available from Stratagene Cloning System). The resulting plasmid was designated pAL601. The analysis of pAL601 with restriction endonucleases revealed that about 7.0 kbp Eco RI fragment was inserted (see FIG. 1).

For about 2 kbp Sma I fragment (i.e., coding region for the esterase gene) of pAL601, the base sequence was determined with PRISM kit and automatic base sequence analyzer 373A (both available from Perkin Elmer Japan). The analysis was carried out with Genetyx-Mac/ATSQ and Genetyx-Mac (both available from Software Kaihatsu). The base sequence of the esterase gene is shown by SEQ ID NO:1 in the Sequence Listing.

In the amino acid sequence (shown by SEQ ID NO:2 in the Sequence Listing) deduced from the base sequence determined, there is a region completely corresponding to the amino acid sequence of SEQ ID NO:3, and the presence of the desired esterase gene on the above DNA fragment was confirmed.

Example 6 (Optical Selectivity I of Esterase)

pAL601 was digested with the restriction endonuclease Sma I and subcloned to give pAL612. The resulting pAL612 was transformed into E. coli strain JM109.

A culture of the transformant E. coli strain JM109/pAL612 thus obtained was grown on 100 ml of LB medium containing 50 mg/l of ampicillin and 50 mg/l of 1 mM isopropyl thio-β-D-galactoside (hereinafter referred to simply as IPTG) at 37° C. for 16 hours, and then harvested by centrifugation at 6000 rpm for 10 minutes to collect the bacterial cell.

The bacterial cells obtained were suspended in 20 ml of 200 mM phosphate buffer. Then, 0.5 g of the methyl ester of (RS)4-hydroxy-3-methyl-2-(2-propenyl)cyclopent-2-en-1-one and 8.0 ml of 50 mM phosphate buffer (pH 7.0) were put in a 100 ml sample bottle, and preheated under stirring with a stirring bar at 40° C. for 10 minutes. To this mixture was added 1.0 ml of the above suspension, and the reaction was effected at 40° C. under stirring with a stirring bar. After 30 minutes, the reaction mixture was taken in a volume of 50 µl, and the reaction was stopped by the addition of 1 ml of ethanol. For blanks, purified water was used instead of the culture, and the test was conducted in the same manner. The rate of decomposition was determined by gas chromatography. As the column for analysis, 10% silicone DC-QF-1, 2.6 m long, was used, and the analysis was carried out with GC-14A (from Shimazu Seisakusho) under the following conditions: column temperature, 150° C.; injection temperature, 170° C.; detection temperature, 170° C.; and detector, FID. The reaction mixture was further extracted with methyl isobutyl ketone, and the extract was examined for optical purity by the HPLC analysis. In the analysis, a column for optical isomer analysis OA-4100 (4.0 mm I.D.× 25 cm) available from Sumika Bunseki Center was used. As the eluent, a mixture of hexane, 1,2-dichloroethane and ethanol at a ratio of 100:20:1 was used. The optical isomer ratio was determined at a flow rate of 1.0 ml/min. with an absorbance at 230 nm as an index.

Based on the results of the above analysis, the rate of hydrolysis and optical selectivity were calculated and are shown in Table 2.

TABLE 2

| Transformant | Rate of hydrolysis (%) | Optical isomer ratio [(S)/(R)] of released 4-hydroxy-3-methyl-2-(2-propenyl)cyclopent-2-en-1-one |
|---|---|---|
| JM109/pAL612 | 45 | 2/98 |

As can be seen from Table 3, E. coli strain JM109/pAL612, which is a transformant containing the inserted 2 kbp Sma I fragment, produces an esterase capable of causing asymmetric hydrolysis of the acetic acid ester of (RS)4-hydroxy-3-methyl-2-(2-propenyl)cyclopent-2en-1-one to produce (R)4-hydroxy-3-methyl-2-(2-propenyl)cyclo-pent-2-en-1-one.

Example 7 (Optical Selectivity II of Esterase)

The acetic acid ester of (RS)4hydroxy-3-methyl-2-(2-propynyl)cyclopent-2-en-1-one was used as the substrate, and the same experiments as described in Example 4 were made. The results are shown in Table 3.

TABLE 3

| Transformant | Rate of hydrolysis (%) | Optical isomer ratio [(S)/(R)] of released 4-hydroxy-3-methyl-2-(2-propynyl)cyclopent-2-en-1-one |
|---|---|---|
| JM109/pAL612 | 40 | 2/98 |

Example 8 (Optical Selectivity III of Esterase)

The acetic acid diester of (RS)-4-hydroxy-2-(7-hydroxyheptyl)-2-cyclopentenone was used as the substrate, and the same experiments as described in Example 4 were made. The results are shown in Table 4. As the buffer, 100 mM phosphate buffer (pH 6.0) was used.

TABLE 4

| Transformant | Rate of hydrolysis (%) | Optical isomer ratio [(S)/(R)] of released 4-hydroxy-2-(7-hydroxyheptyl)-2-cyclopentenone |
|---|---|---|
| JM109/pAL612 | 24 | 0/80 |

The rate of decomposition was determined by gas chromatography for the acetic acid diester of 4-hydroxy-2-(7-hydroxyheptyl)-2-cyclopentenone. As the column for analysis, a 10% silicone DC-QF-1, 2.6 m long,. was used, and the analysis was carried out under the following conditions: column temperature, 240° C. and injection temperature, 260° C. The reaction mixture was further extracted with methyl isobutyl ketone, and the extract was examined for optical purity by the HPLC analysis. In the analysis of 4-hydroxy-2-(7-hydroxyheptyl)-2-cyclopentenone, two columns for optical isomer analysis OA-4500 available from Sumika Bunseki Center were used in connected form. As the eluent, a mixture of hexane, 1,2-dichloroethane and ethanol at a ratio of 100:4:4 was used. The optical isomer ratio was determined at a flow rate of 1.5 ml/min. with an absorbance at 235 nm as an index.

Example 9 (Optical Selectivity IV of Esterase)

The acetic acid ester of (RS)4-hydroxy-2-(6-methoxycarbonylhexyl)-2-cyclopentenone was used as the substrate, and the same experiments as described in Example 4 were made. The results are shown in Table 5.

TABLE 5

| Transformant | Rate of hydrolysis (%) | Optical isomer ratio [(S)/(R)] of released 4-hydroxy-2-(6-methoxycarbonylhexyl)-2-cyclopentenone |
|---|---|---|
| JM109/pAL612 | 30 | 9/91 |

The rate of decomposition was determined by gas chromatography. As the column for analysis, 10% silicone DC-QF-1, 2.6 m long, was used, and the analysis was carried out under the following conditions: column temperature, 240° C. and injection temperature, 260° C. The reaction mixture was further extracted with methyl isobutyl ketone, and the extract was examined for optical purity by the HPLC analysis. In the analysis of 4-hydroxy-2-(6-methoxycarbonylhexyl)-2-cyclopentenone, a column for optical isomer analysis OA4500 available from Sumika Bunseki Center was used. As the eluent, a mixture of hexane, 1,2-dichloroethane and ethanol at a ratio of 100:20:1 was used. The optical isomer ratio was determined at a flow rate of 1 ml/min. with an absorbance at 235 nm as an index.

As described above, the present invention made it possible to provide a gene coding for an esterase capable of acting upon an organic carboxylic acid ester of a cyclopentenolone of formula I for asymmetric hydrolysis of the ester to produce the cyclopentenolone of formula I in (R)-form with high optical purity.

What is claimed is:

1. An isolated esterase having the following characteristics:

a) a molecular weight, determined by SDS-PAGE, of about 38 kilodaltons;

b) an isoelectric point of 6.0;

c) an optimum temperature of about 60° C.;

d) an optimum pH of about 5 to about 7;

e) capable of using asymetric hydrolysis of an organic carboxylic ester of a cyclopentenolone of formula (I):

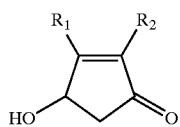

[I]

wherein, $R_1$ is hydrogen or methyl, and $R_2$ is $C_1$–$C_{10}$ alkyl, $C_2$–$C_{10}$ alkenyl, $C_2$–$C_{10}$ alkynyl, $C_1$–$C_4$ haloalkyl, a $C_5$–$C_9$ aliphatic hydrocarbon moiety which may be optionally protected on the terminal hydroxyl group thereof, or a $C_5$–$C_9$ fatty acid residue which may be optionally protected on the terminal carboxyl group thereof, in (R)-form and f) comprises an amino acid sequence of SEQ ID NO:2.

2. An isolated esterase capable of the optical resolution of a cyclopentenolone of Formula I:

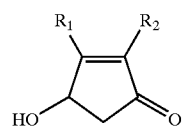

[I]

wherein $R_1$ is hydrogen or methyl, and $R_2$ is $C_1$–$C_{10}$ alkyl, $C_2$–$C_{10}$ alkenyl, $C_2$–$C_{10}$ alkynyl, $C_1$–$C_4$ haloalkyl, a $C_5$–$C_9$ aliphatic hydrocarbon moiety which may be optionally protected on the terminal hydroxyl group thereof, or a $C_5$–$C_9$ fatty acid residue which may be optionally protected on the terminal carboxyl group thereof, by allowing the esterase to act upon an organic carboxylic acid ester of the cyclopentenolone of formula (I) for asymmetric hydrolysis of the ester, wherein said esterase is selected from the group consisting of:

(1) an esterase comprising the amino acid sequence of SEQ ID NO:2, (2) an esterase comprising 363 amino acids and being coded for by a polynucleotide having:

(a) a recognition sequence for the restriction endonuclease for SalI at a point equivalent to nucleotides 537–542 of SEQ ID NO:1 in said polynucleotide, (b) no recognition sequence for the restriction endonuclease SmaI and XhoI, and (c) a full complement of a nucleotide sequence hybridizing to SEQ ID NO:1 under conditions of 6×SSC (standard saline citrate), 0.5% (w/v) SDS (sodium dodecyl sulfate), 100 μg/ml salmon sperm DNA, 63° C.;

(3) an esterase that is coded by a polynucleotide, said polynucleotide being contained in the deposited strain FERM BP-5740,
(4) an esterase that is coded by a polynucleotide comprising a base sequence of SEQ ID NO:1; and
(5) an esterase that is coded by a polynucleotide coding for a region in SEQ ID NO:2 of which N-terminal amino acid sequence is the same as defined in SEQ ID NO:3 which is identical to residues 44–58 of SEQ ID NO:2 and is a full complement to a nucleotide sequence hybridizing to SEQ ID NO:1 under conditions of 6×SSC (standard saline citrate), 0.5% (w/v) SDS (sodium dodecyl sulfate), 100 μg/ml salmon sperm DNA, 63° C.

3. The esterase of claim 1 or 2 in the form of a crude enzyme preparation.

4. The esterase of claim 1 or 2 in the form of a purified esterase.

5. The esterase of claim 1 or 2 which is immobilized on a carrier.

6. The esterase of claim 1 or 2 in the form of a cell-free preparation.

* * * * *

SEQUENCE LISTING

<160> NUMBER OF SEQ ID NOS: 4

<210> SEQ ID NO 1
<211> LENGTH: 1089
<212> TYPE: DNA
<213> ORGANISM: Burkholderia cepacia

<400> SEQUENCE: 1

```
atgagcagat cgatacgagc gaaggcagtg gcgaccgtgg tggcgatcaa cgcggccccg        60
gccgcgagtg ttggaaccgt tctggccatg tcgctggccg gcgcacaggc cgcttccgcc       120
gcgacgaccg ccgttgacga ctacgcggcg acccggtacc cgatcattct cgtgcacggg       180
ctgaccggca ccgacaagta cggtggcgtc gtcgagtact ggtatcgcat tccggaggac       240
ctgcgggcgc acggcgcggc ggtatacgtt gccaacctgt ccggcttcca gagcgacgat       300
ggcccgaacg ggcgtggcga gcaattgctt gcattcgtga agcaggtgct cgcggcgacg       360
ggcgcgcaga aggtgaatct gatcggccat agccagggcg gcctgacatc gcgttatgtt       420
gcgtccgttg caccggaact ggtcgcatcg gtgacgacga tcagtacgcc gcactggggc       480
tcgcaattcg cggacttcgt ccagcaactg ttgcagacgg acccgaccgg cctgtcgtcg       540
accgtgctcg gcgcattcgc gaatgcgctc ggcacgttga cgagcagcaa cttcaatacg       600
aaccagaatg cgattcaggc gttgtcggtg ctgacgacgg caaaggccgc cgcatacaac       660
cagaaattcc cgagcgccgg tctcggtgcg ccgggctcgt gtcaaaccgg cgcgccaacg       720
gagactgtcg gcggcaatac gcatctgctt tattcgtggg gcggcacggc gatccagccg       780
acagcgacgg tggccggcgt gacagggggcc gtcgatacga gcgtgagcgg ggtcaccgat       840
```

-continued

```
ccggcgaacg cgctcgatcc gtcaacgctg gcactcctcg gcagcggcac ggtgatgatc    900
aatcgcagcg ccggtccgaa cgatggcgtc gtgtcgcaat gcagcgcgcg gtttggccag    960
gtgctcggca cgtatcactg gaatcacacc gatgcgatca accagatcct cggcgtgctc   1020
ggcgcgaatg tggaggatcc ggttgcggta atccgcacgc acgcgaaccg gttgaagaat   1080
caaggcgtg                                                            1089
```

<210> SEQ ID NO 2
<211> LENGTH: 363
<212> TYPE: PRT
<213> ORGANISM: Burkholderia cepacia

<400> SEQUENCE: 2

```
Met Ser Arg Ser Ile Arg Ala Lys Ala Val Ala Thr Val Val Ala Ile
 1               5                  10                  15

Asn Ala Ala Pro Ala Ala Ser Val Gly Thr Val Leu Ala Met Ser Leu
            20                  25                  30

Ala Gly Ala Gln Ala Ala Ser Ala Ala Thr Thr Ala Val Asp Asp Tyr
        35                  40                  45

Ala Ala Thr Arg Tyr Pro Ile Ile Leu Val His Gly Leu Thr Gly Thr
    50                  55                  60

Asp Lys Tyr Gly Gly Val Val Glu Tyr Trp Tyr Arg Ile Pro Glu Asp
 65                  70                  75                  80

Leu Arg Ala His Gly Ala Ala Val Tyr Val Ala Asn Leu Ser Gly Phe
                85                  90                  95

Gln Ser Asp Asp Gly Pro Asn Gly Arg Gly Glu Gln Leu Leu Ala Phe
           100                 105                 110

Val Lys Gln Val Leu Ala Ala Thr Gly Ala Gln Lys Val Asn Leu Ile
       115                 120                 125

Gly His Ser Gln Gly Gly Leu Thr Ser Arg Tyr Val Ala Ser Val Ala
   130                 135                 140

Pro Glu Leu Val Ala Ser Val Thr Thr Ile Ser Thr Pro His Trp Gly
145                 150                 155                 160

Ser Gln Phe Ala Asp Phe Val Gln Gln Leu Leu Gln Thr Asp Pro Thr
               165                 170                 175

Gly Leu Ser Ser Thr Val Leu Gly Ala Phe Ala Asn Ala Leu Gly Thr
           180                 185                 190

Leu Thr Ser Ser Asn Phe Asn Thr Asn Gln Asn Ala Ile Gln Ala Leu
       195                 200                 205

Ser Val Leu Thr Thr Ala Lys Ala Ala Ala Tyr Asn Gln Lys Phe Pro
   210                 215                 220

Ser Ala Gly Leu Gly Ala Pro Gly Ser Cys Gln Thr Gly Ala Pro Thr
225                 230                 235                 240

Glu Thr Val Gly Gly Asn Thr His Leu Leu Tyr Ser Trp Gly Gly Thr
               245                 250                 255

Ala Ile Gln Pro Thr Ala Thr Val Ala Gly Val Thr Gly Ala Val Asp
           260                 265                 270

Thr Ser Val Ser Gly Val Thr Asp Pro Ala Asn Ala Leu Asp Pro Ser
       275                 280                 285

Thr Leu Ala Leu Leu Gly Ser Gly Thr Val Met Ile Asn Arg Ser Ala
   290                 295                 300

Gly Pro Asn Asp Gly Val Val Ser Gln Cys Ser Ala Arg Phe Gly Gln
305                 310                 315                 320
```

```
Val Leu Gly Thr Tyr His Trp Asn His Thr Asp Ala Ile Asn Gln Ile
                325             330             335

Leu Gly Val Leu Gly Ala Asn Val Glu Asp Pro Val Ala Val Ile Arg
            340             345             350

Thr His Ala Asn Arg Leu Lys Asn Gln Gly Val
        355             360

<210> SEQ ID NO 3
<211> LENGTH: 15
<212> TYPE: PRT
<213> ORGANISM: Burkholderia cepacia

<400> SEQUENCE: 3

Ala Val Asp Asp Tyr Ala Ala Thr Arg Tyr Pro Ile Ile Leu Val
  1               5                  10                  15

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: modified_base
<222> LOCATION: (3)..(42)
<223> OTHER INFORMATION: any n = i
<220> FEATURE:
<223> OTHER INFORMATION: any y = t or c

<400> SEQUENCE: 4
gcngtngayg actaygcngc nacncgntay ccnatyatnc tngt                    44
```